United States Patent [19]

Wiegert

[11] 4,069,250
[45] Jan. 17, 1978

[54] SUBSTITUTED 2,4,6-TRIIODOISOPHTHALAMIC ACIDS

[75] Inventor: Philip E. Wiegert, St. Louis, Mo.

[73] Assignee: Mallinckrodt, Inc., Mo.

[21] Appl. No.: 676,169

[22] Filed: Apr. 12, 1976

Related U.S. Application Data

[63] Continuation of Ser. No. 479,716, June 17, 1974, abandoned.

[51] Int. Cl.² .............. C07C 103/32; A61K 29/02
[52] U.S. Cl. ..................... 260/519; 260/515A; 424/5; 260/501.16; 260/307 R; 560/46
[58] Field of Search .............. 260/519; 424/5

[56] References Cited

U.S. PATENT DOCUMENTS 3,622,616  11/1971  Guerbet et al. .............. 260/519
3,701,771  10/1972  Almen et al. ................ 260/519
3,702,866  11/1972  Salvesen et al. ............. 260/519
3,914,294  10/1975  Bernstein .................... 424/5
4,001,323   1/1977  Feleder et al. ............... 424/5

Primary Examiner—James O. Thomas. Jr.
Assistant Examiner—James H. Reamer
Attorney, Agent, or Firm—R. J. Klostermann

[57] ABSTRACT

Certain N-[poly(hydroxyalkyl)alkyl], 2,4,6-triiodoisophthalamic acids are useful as x-ray contrast agents. A representative compound has the structure

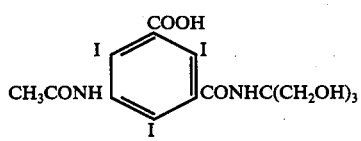

13 Claims, No Drawings

SUBSTITUTED 2,4,6-TRIIODOISOPHTHALAMIC ACIDS

This is a continuation, of application Ser. No. 479,716, filed June 17, 1974 now abandoned.

BACKGROUND OF THE INVENTION

This invention relates to the field of organic chemistry, and more particularly to novel triiodoisophthalamic acid derivatives useful as X-ray contrast agents.

Many 2,4,6-triiodobenzoic acid derivatives have been proposed for use as X-ray contrast agents. These include, as a subgroup, many 2,4,6-triiodoisophthalamic acid derivatives. Among the latter, certain N-hydroxyalkyl-2,4,6-triiodoisophthalamic acids have been disclosed. For example, both Guerbet et al. U.S. Pat. No. 3,622,616, and Salvesen et al. U.S. Pat. No. 3,702,866 disclose 5-acetamido-N-(2-hydroxyethyl)-2,4,6-triiodoisophthalamic acid. In addition, Salvesen et al. also disclose the compound, N-(3-acetamido-5-carboxy-2,4,6-triiodobenzoyl)-N-methylglucamine, which may also be designated 5-acetamdio-N-(D-gluco-1-deoxy-2,3,4,5,6-pentahydroxyhexyl)-2,4,6-triiodo-N-methylisophthalamic acid.

Further, Almen et al. (U.S. Pat. No. 3,701,771) disclose a considerable number of non-ionic N-(2,4,6-triiodobenzoyl)-amines said to be useful as X-ray contrast agents in the cerebrospinal cavities, including one (compound 41) derived from tris(hydroxymethyl) aminomethane. This compound is designated as N-[3-N-methylacetamido-5-N-(beta-hydroxyethyl)-acetamido-2,4,6-triiodobenzoyl] N-[tris-(hydroxymethyl)-methyl]-amine This compound was reported to have a rather low water solubility (0.86%) although many other compounds in the series were disclosed to be relatively highly soluble in water.

The use, as x-ray contrast media, of aqueous solutions of salts of various 2,4,6-triiodoisophthalamic and other 2,4,6-triiodobenzoic acids with sodium, calcium, magnesium and alkanolamines, such as ethanolamine, diethanolamine and N-methylglucamine, is well known to those skilled in the art.

SUMMARY OF THE INVENTION

Among the objects of the invention may be mentioned the provision of new isophthalamic acid derivatives; the provision of new 2,4,6-triiodoisophthalamic acid compounds; the provision of compounds of the type indicated which are useful for the preparation of roentgenographic contrast media; the provision of new m-nitro-, m-amino- and m-hydroxyisophthalic acid derivatives useful as intermediates in the preparation of such compounds; and the provision of methods of preparing such compounds. Other objects will be in part apparent and in part pointed out hereinafter.

The present invention is directed to certain 2,4,6-triiodoisophthalamic acids wherein the nitrogen of the isophthalamic acid amide function is attached to a carbon which, in turn is attached to at least two functions selected from the group consisting of hydroxy-(lower alkyl) and lower alkoxyalkyl functions, the ring being further substituted in the 5-position by an amino or hydroxy function or by a TIBA detoxifying/solubilizing function (as defined hereinafter) derived therefrom. The invention also includes salts of such acids and aycl halide and ester derivatives thereof. The salts, with pharmaceutically acceptable cations, of the acids containing a TIBA detoxifying/solubilizing function in the 5-position are useful in the prepartion of X-ray contrast media intended primarily for intravascular administration. Other salts, such as ammonium salts, are useful as intermediates. Esters of the carboxy function of the isophthalamic acid are useful in X-ray contrast media intended primarily for use in instillation procedures. Acyloxy esters of hydroxyalkyl functions occurring in the substituted isophthalamic acids are primarily useful as intermediates.

The invention further includes 5-nitro, 5-amino and 5-hydroxyisophthalamic acids wherein the isophthalamic acid amide function is substituted as defined above. These uniodinated N,5-disubstituted isophthalamic acids are useful as intermediates in the preparation of the iodinated compounds defined above.

The patent and journal literature is replete with disclosures of derivatives of 2,4,6-triiodobenzoic acid (hereinafter sometimes called TIBA) which are useful as X-ray contrast agents because of their low toxicity and high water solubility. The preparation of such compounds had its inception in the pioneering work of V. H. Wallingford (U.S. Pat. No. 2,611,786), who first prepared 3-acetamido-TIBA and its homologs.

Developments in this field have recently been comprehensively summarized by G. B. Hoey, P. E. Wiegert and R. D. Rands, Jr., "Organic Iodine Compounds as X-Ray Contrast Media," in International Encyclopedia of Pharmacology and Therapeutics, Section 76, "Radiocontrast Agents," P. K. Knoefel, Section Editor; Pergamon Press; Vol. 1, pp. 23–40, 54–73 (1971). Hoey et al. apply the term "solubilizing and detoxifying groups" to denote generically a substantial number of functional groups whose occurrence in the meta-position in a 2,4,6-triiodobenzoic acid has come to be associated with TIBA derivatives that are relatively highly water soluble and relatively nontoxic.

As is pointed out by Hoey, et al., in a landmark discovery V. H. Wallingford found that sodium 3-acetamido-2,4,6-triiodobenzoate (sodium acetrizoate) possessed two outstanding properties which peculiarly adapted it to use as an x-ray contrast agent; its water solubility was unexpectedly high and its toxicity was unexpectedly low. Thus was discovered the first TIBA detoxifying/solubilizing function, viz., the acetamido group. 3-Acetamido-2,4,6-triiodobenzoic acid contains one acetamido substituent meta to the carboxyl. The second meta position is unsubstituted. Within a relatively brief period following Wallingford's initial discovery, three groups of investigators independently discovered that substitution of a second acetamido group in the vacant meta position created a new compound, 3,5-diacetamido-2,4,6-triiodobenzoic acid (diatrizoic acid) with still further reduced toxicity as compared with acetrizoic acid. (See, for example, Schering A.G. German Appln. Sch 11647/1965; A. A. Larsen, et al., J. Am. Chem. Soc. 78:3210/1956;Mallinckrodt Chem. Wks. Br. Spec. 782,313/1957).

Since the work outlined above was reported many other fully substituted 2,4,6-triiodbenzoic acids have been prepared and evaluated as water soluble x-ray contrast agents. This has resulted in the identification of many functional groups whose occurrence in the 5-position of a 3-acetamido-2,4,6-triiodobenzoic acid results in a fully substituted 2,4,6-triiodobenzoic acid whose sodium salt is highly water soluble and relatively nontoxic.

Adapting the terminology of Hoey et al., we define, for the purposes of this disclosure, a TIBA detoxifying-/solubilizing function as a functional group whose occurrence in the 5-position of a 3-acetamido-2,4,6-triiodobenzoic acid results in a fully substituted 2,4,6-triiodobenzoic acid whose sodium salt is highly water soluble and relatively non-toxic. By "highly water soluble" we mean having a water solubility of the order of 45% (w/v) or greater. By "relatively non-toxic" we mean having an acute intravenous $LD_{50}$ in white mice of the order of 5 grams or more of compound per kilogram of animal body weight.

It is well established that the most practical syntheses of 2,4,6-triiodoisophthalamic acid compounds involve the use of an intermediate which contains, in the 5-position, a group, such as the amino or hydroxyl group, which activates the aromatic nucleus toward iodination. Therefore, as a practical matter, in the triiodoisophthalamic acids the permissible TIBA detoxifying-/solubilizing functions at the 5-position are limited to those which are derived from activating functional groups, such as the amino and hydroxyl groups.

A substantial number of TIBA detoxifying/solubilizing functions derived from amino or hydroxyl groups have been identified in the prior art. Following is a partial list: lower acylamino, e.g. acetamido; N-(lower alkyl)-lower acylamino, e.g. N-methylacetamido; hydroxy lower acylamino, e.g. hydroxyacetamido; lower (acylaminoacylamino, e.g. aceturamido; N-(hydroxy lower alkyl) lower acylamido, e.g. N-(2-hydroxyethyl)-acetamido and N-(2,3-dihydroxypropyl)-acetamido; lower alkoxy-lower acylamino, e.g. methoxyacetamido; lower alkylsulfonamido, e.g. methylsulfonamido; ureido, 3-lower alkyl ureido, e.g. 3-methylureido; 3,3-bis(lower alkyl)ureido, e.g. 3,3-dimethylureido; and lower alkoxy, e.g. methoxy. Other such functions will be obvious to those skilled in the art. Certain end product compounds of the invention may be conveniently portrayed by means of the following structural formula:

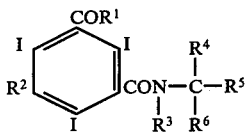

wherein
R' is hydroxy, lower alkoxy or OM, M being a pharmaceutically acceptable cation,
$R^2$ is a TIBA detoxifying/solubilizing function derived from an amino function,
$R^3$ and $R^4$ are selected from the group consisting of hydrogen, lower alkyl, hydroxy (lower alkyl) and lower alkoxyalkyl functions, and $R^5$ and $R^6$ are selected from the group consisting of hydroxy (lower alkyl) and lower alkoxyalkyl functions.

Preferred functions at $R^2$ are the acetamido, N-methylacetamido and methoxyacetamido functions. Preferred functions at $R^3$-$R^6$ are as follows:
$R^3$ - hydrogen;
$R^4$ - methyl or hydroxymethyl;
$R^5$ and $R^6$ - hydroxymethyl.

The novel compounds of the invention are derived from poly (hydroxyalkyl)alkyl amines wherein the amino function is attached to a carbon atom which, in turn, is attached to at least two hydroxy-(lower alkyl) functions. One readily available amine of this type is tris(hydroxymethyl)aminomethane, which is also known by a variety of coined names, including TRIS, THAM and tromethamine. Another is 2-amino-2-methyl-1,3-propanediol.

In another aspect, the invention relates to methods of preparing the novel compounds of the invention. For example the compounds represented by the structure set forth above may be prepared by the general method outlined below. A 5-nitroisophthalic is condensed with a poly (hydroxyalkyl)alkyl amine. In the case wherein $R^3$ is hydrogen, the 5-nitroisophthalic acid derivative may be a lower alkyl mono-ester, such as monomethyl 5-nitroisophthalate, the reaction may be carried out in an aqueous or alcoholic medium, and the product will be a 5-nitro-N-[poly(hydroxyalkyl)alkyl]isophthalamic acid. When $R^3$ is not hydrogen, the poly(hydroxyalkyl)alkyl amine will a secondary amine and successful condensation will ordinarily require that the isophthalic acid derivative be a monoester monoacyl halide, i.e., a 3-(lower alkoxy)carbonyl-5-nitrobenzoyl halide. The reaction will then ordinarily be carried out in a suitable non-aqueous polar solvent, such as dimethylformamide, in the presence of a base such as potassium carbonate. Non-polar or aqueous solvents may also be used. The product will then be a 5-nitro-N-[poly(hydroxyalkyl)alkyl]isophthalamic acid, lower alkyl ester, which may be hydrolyzed to form the free acid. This 5-nitroisophthalamic acid derivative is then reduced to the corresponding 5-amino-N-[poly(hydroxyalkyl)alkyl]isophthalamic acid. The reduction is ordinarily accomplished by catalytic hydrogenation of an alcoholic solution of the free acid or of an aqueous solution of the sodium salt, in the presence of a suitable supported noble metal catalyst, such as 5% Pd on charcoal. Conventional chemical reducing systems, such as iron/acetic acid or Zn/HCl may also be used. Alternatively, the nitro group may be reduced to the corresponding amine before the ester is hydrolyzed to the free acid. The 5-amino-N-[poly(hydroxyalkyl)alkyl]isophthalamic acid obtained by any of the above routes may then be iodinated to the corresponding 2,4,6-triiodo compound. Preferably the iodination is carried out in an acidic solution of the sodium salt utilizing sodium iododichloride as the iodinating agent. The resulting 5-amino-2,4,6-triiodo-N-[poly(hydroxyalkyl)alkyl] isophthalamic acid may then be acylated by means of an acid anhydride, acyl halide or other acylating agent. This ordinarily results in acylation, not only of the amino function, but also of any free hydroxy functions in the molecule, thus bringing about the formation of a 5-acylamino-2,4,6-triiodo-N-[poly (acyloxyalkyl)alkyl]isophthalamic acid. The acyloxy ester functions may then be hydrolyzed in weakly alkaline solution to form a solution of a salt of the corresponding 5-acylamino-2,4,6-triiodo-N-[poly(-hydroxyalkyl)alkyl]isophthalamic acid. Acidification of the solution then causes precipitation of the free acid, which may be purified by known procedures, such as reprecipitation, recrystallization, etc.

If it is desired that the final product contain alkoxy functions in any of $R^3$-$R^6$, the corresponding precursor hydroxy functions in the poly(hydroxyalkyl)alkyl amine staring material may most conveniently be etherified prior to condensation of the amine with the nitrobenzoyl halide. The resulting 5-nitro-N-[poly (alkoxyalkyl)alkyl]isophthalamic acid, lower alkyl ester may then be hydrogenated, iodinated and acylated as outlined above. Those compounds of the invention wherein $R^2$ is an hydroxy function or a TIBA detoxifying/solubilizing function derived therefrom are prepared by a comparable series of reactions beginning with the condensation of a suitable 5-hydroxyisophthalic acid derivative, e.g., a lower alkyl mono-ester or a monoester monoacyl halide, with a poly(hydroxyalkyl) alkyl amine, to form a 5-hydroxy-N-[poly(hydroxyalkyl)alkyl]-isophthalamic acid, followed by iodination to form a 5-hydroxy-2,4,6-triiodo-N-[poly(hydroxyalkyl)alkyl]isophthalamic acid. Alkylation of the hydroxy functions may then be accomplished by reaction with a suitable alkylating agent, such as dimethyl sulfate (see, for example, Wiegert U.S. Pat. No. 2,939,881) or glycerol alpha monochlorohydrin (see, for example, Wiegert et al. U.S. Pat. No. 2,963,474).

DETAILED DESCRIPTION

Certain of the terms used in the general description set forth above are defined more fully below.

The terms "lower alkyl" and "lower alkoxy" mean, respectively, an alkyl or alkoxy group containing one to six carbon atoms.

The term "hydroxy (lower alkyl)" embraces monohydroxyalkyl and polyhydroxyalkyl groups and includes structures such as the following:

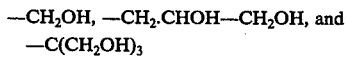

The term "lower alkoxyalkyl" means an alkyl group substituted with one or more alkoxy groups, the alkoxyalkyl group containing a total of 2–6 carbon atoms.

The invention, as generally described above, is further illustrated by the following examples.

EXAMPLE 1

N[tris(hydroxymethyl)methyl]-5-nitroisophthalamic Acid

Methyl hydrogen 5-nitroisophthalate, 22.9 lbs. (46.0 grammoles--7% $H_2O$), was slurried in 8.8 gal. of water. Tris(hydroxymethyl)aminomethane (226.2 gram-moles) 60.3 lbs. was added in two portions, 15 min. apart. The temperature dropped to 15° C. The slurry was warmed to a temperature of 43° C. to complete dissolution. The solution was cooled to 30°–32° C. and allowed to stand overnight (19 hrs.). At that time reaction was complete, as judged by thin-layer chromatography (TLC), using benzene:methylethylketone (MEK):88% formic acid (60:25:20) and isobutyl alcohol:isopropyl alcohol:NH$_4$OH (100:40:50) systems. The solution was pumped into diluted sulfuric acid (1.52 gal. conc. $H_2SO_4$ + 3.59 gal. $H_2O$) in about 2–4 min. The temperature rose from 8° to 45° C. and crystallization began in 5–10 min. After stirring for 1 hour without cooling and one hour with cooling, the product was collected, reslurried in 7.2 gal. of ice water, collected again, and dried overnight at 60° C. Yield of crude product, 28.5 lbs., (92.4%), m.p. 173.5°–175.9° C. TLC using the systems described above showed some 5-nitroisophthalic acid impurity.

The product from above was dissolved in 520 lbs. of methanol at 55°–57° C. and the solution was concentrated until 378 lbs. of methanol remained. The solution was cooled, benzene (464 lbs.) was added, and the mixture was cooled overnight. The product was collected, reslurried in 10 gal. of methanol/benzene (1:3) and collected again. Yield 20.29 lbs., m.p. 175°–177° C.

The preparation was repeated on the same scale; a yield of 20.59 lbs. was obtained in the second run.

Both batches were combined (40.88 lbs.), dissolved in 41 gal. of 5% NaHOO$_3$ solution, the pH was adjusted to 5 with acetic acid and the solution was treated with 1.64 lbs. of charcoal at 25° C. The charcoal was filtered off and the filtrate was added to 9.3 gal. of 10% $H_2SO_4$ (w/v) and 8.4–9.0 gal. of $H_2O$. After one-fifth to one-fourth of the filtrate had been added to the $H_2SO_4$, precipitation started. The slurry was cooled 45 min. and the product was collected and washed with ice water. The product was reslurried in 15 gal. of ice water, collected, and dried at 65°–70° C. Yield, 34.5 lbs., m.p. 180.5°–181.9°.

The above product was recrystallized from water and dried at 65°–70° C. Yield 31.05 lbs. (48.6%); m.p. 184.9–185.9, N.E. found/theory 317.4/314.2. Only a trace impurity of 5-nitroisophthalic acid could be seen in the two TLC systems described above.

An analytical sample was further dried at 56° C./2 Torr. for 16 hours. Anal. Calcd. for $C_{12}H_{14}N_2O_8$: C, 45.88; H, 4.45; N, 8.91; N.E. 314.3. Found: C, 45.92; H, 4.56; N, 9.09; N.E. 314.1.

EXAMPLE 2

5-Amino-N[tris(hydroxymethyl)methyl]-isophthalamic Acid, Sodium Salt

5-Nitro-N-[tris(hydroxymethyl)methyl]-isophthalamic acid (314 g., 1.0 mole) was dissolved in water with the aid of NaOH, the pH was adjusted to 6.3–6.5, and the solution was treated with 2.67 g. of 5% Pd/C and 6.67 g. of charcoal for 35 minutes at 25°–30° C. The charcoal was removed, the solution was diluted to 1250 ml., and 6.5 g. of 5% Pd/C was added. Catalytic hydrogenation of the nitro group was carried out on a Parr shaker. Hydrogen uptake was quantitative in 4 hours, but shaking was continued overnight. The catalyst was removed, and the solution of 5-amino-N-[tris(hydroxymethyl)methyl] isophthalamic acid, sodium salt, was used promptly in the iodination step (Example 3) without isolation of the amine.

Alternatively, the hydrogenation may be carried out on a solution of the 5-nitro-[tris(hydroxymethyl)methyl]isophthalamic acid in methano or other alcohol.

EXAMPLE 3

5-Amino-N-[(trishydroxymethyl)methyl]-2,4,6-triiodoisophthalamic Acid

A solution of freshly prepared 5-amino-N[(trishydroxymethyl) methyl]isophthalamic acid, sodium salt, (1.0 mole) in 1250 ml. of water (Example 2), was diluted to 3613 ml., and hydrochloric acid (187 ml.) was added. NaICl$_2$ (2.34N) was used as the iodinating agent. A total of 1410 ml. (10% excess) was added at 45° C. in three equal portions. The reaction mixture was stirred 15–20 minutes between additions. Progress of the iodination was followed by titration with thiosulfate. When the iodine uptake was 66% (about 2 hrs. at 45° C.) the temperature was slowly increased to 83° C. and the solution was diluted to twice its volume. After about 2–3 hrs. more at 83°, the iodine uptake was 98.6%. The slurry was stirred overnight at 25° C. and the product was collected in the morning (iodine uptake was 100%), reslurried in 1 l. of water with a small amount of NaHSO$_3$ present, filtered, and dried. Yield, 524 g.

The crude product was recrystallized from 2.6 l. of ethanol. (Specially denatured alcohol, Formula 2B).

Charcoal (35 g.) was used to decolorize the solution. The product crystallized from SD alcohol 2B in thick fluffy crystals. The solid was collected, reslurried in 800 ml. of SD alcohol 2B, collected, and air dried. It was then dissolved in 2 l. of water with NaOH, adjusted to pH 4.5 with acetic acid, and added to 1.1 l. of 5% HCl. The precipitate of 5-amino-N-[tris(hydroxymethyl) methyl]-2,4,6-triiodoisophthalamic acid was collected, reslurried in 700 ml. of water, collected again, and dried at 70° C. Yield, 362 g. (54.7%). Anal. Calcd. for $C_{12}H_{13}I_3N_2O_8$: C, 21.77; H, 1.96; I, 57.52; N, 4.23; N.E. 662.0. Found: C, 21.78; H, 2.25; I, 55.60; N, 4.03; N.E. 665.8.

The sodium salt of 5-amino-N-[tris-(hydroxymethyl)-methyl]-2,4,6-triiodoisophthalamic acid has a water solubility of approximately 80% (w/v).

EXAMPLE 4

The procedure described below resulted in the formation of two different compounds, identified, respectively, as A. 5-Acetamido-N-[tris(hydroxymethyl)-methyl]-2,4,6-triiodoisophthalamic Acid
B. 3-Acetamido-5-[(4,4-bis(hydroxymethyl)-2-oxazolinyl]-2,4,6-triiodobenzoic Acid

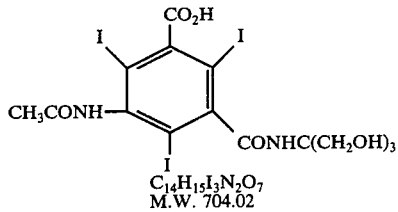

$C_{14}H_{15}I_3N_2O_7$
M.W. 704.02

A

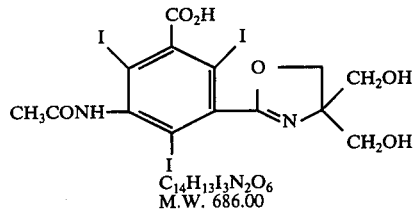

$C_{14}H_{13}I_3N_2O_6$
M.W. 686.00

B

5-Amino-2,4,6-triiodo-N-[tris(hydroxymethyl)methyl]-isophthalamic acid (10 g.; 0.0151 mole), was suspended in 27.2 ml. of acetic anhydride at 29° C. Sulfuric acid (1.8 ml.) was added in one portion. The temperature rose immediately but was held to a maximum of 49° C. with an ice bath. The pink solution was stirred at 35° –40° for 3½ hours. Water was then slowly added with ice-bath cooling and stirring. A maximum temperature of 31° C. was reached. A total of 120 ml. of water was added which precipitated a pink gum. The gum was collected and the filtrate was air evaporated leaving an oil. The gum and oil were combined and dissolved in 55 ml. of water with 37 ml. of ammonium hydroxide solution. This solution of the ammonium salts of the acetoxy derivatives of compounds A and B was warmed at 67° –76° C. for 2 hours while $NH_3$ gas was bubbled to hydrolyze the acetate ester functions. The solution was then concentrated at 80°–100° C./2 mm. The resulting pink solid was dissolved in 30 ml. $H_2O$ and added rapidly at 26° C. to 10% HCl (30 ml.) with stirring and occasional scratching. No precipitate formed until about one-third of the solution had been added. The crystallizing solution was cooled in an ice bath with stirring for one-half hour, then filtered. The first crop that precipitated, 6.67 g., was mainly 3-acetamido-5-[4,4-bis(hydroxymethyl)-2-oxazolinyl]-2,4,6-triiodobenzoic acid (B). Upon standing overnight, 2.39 g. of the desired tris-hydroxymethyl derivative (A) precipitated. Most of this (2.12 g.) was dissolved in 10 ml. of $H_2O$ with NaOH, adjusted to pH 5 with acetic acid and treated with charcoal, (0.25 g) for one-half hour and filtered. The solution was added in one portion to 5 ml. of concentrated hydrochloric acid at 25° C. with stirring. Initially, no precipitate formed but after stirring for 45 min., the product separated and was collected; yield 1.73 g. (16.3%). TLC, benzene-methylethylketone-formic acid (60:25:25) showed one main spot (A) with a trace of the oxazolinyl compound (B) and in isobutyl alcohol-isopropyl alcohol-ammonium hydroxide (100:40:50) one spot (A) with two trace impurities with greater RF values. The NMR and IR spectra were in agreement with the assigned structure (A); m.p. 280°–283° C. (dec.).

Anal. Calcd. for $C_{14}H_{15}I_3N_2O_7$: C, 23.88%; H, 2.15%; I, 54.08%; N.E., 704.0. Found: C, 23.95%; H, 2.23%; I, 53.40%.
N.E. 700.4.

EXAMPLE 5

5-Acetamido-N-[tris(hydroxymethyl)-methyl]-2,4,6-triiodoisophthalamic Acid

5-Amino-N-[tris(hyroxymethyl)methyl]-2,4,6-triiodoisophthalamic acid (250 g.; 0.378 mole) was added in 5 portions to a mixture of acetic anhydride (680 ml.) and sulfuric acid (1.8 ml.) at 45° C. The temperature was held in the range 40°–52° C. During the addition of the last two portions of amine, the product began to crystallize. The slurry was stirred for one hour at 55°–60° C., then colled to 10° C. and water (1250 ml.) was then slowly added with ice-bath cooling and stirring. A maximum temperature of 35° C. was reached. The slurry was stirred b 15 minutes and the preciptated 5-acetamido-N-[tris(acetoxymethyl)methyl]-2,4,6-triiodoisophthalamic acid was collected, reslurried in 500 ml. of water, collected again, and dissolved in 1 liter of water and 925 ml. of ammonium hydroxide solution. The resulting solution was heated at 65°–70° C. for 2 hrs., to hydrolyze the acetate esters, then the solution was evaporated to dryness under reduced pressure. This residue was dissolved in 600 ml. of water and added to 750 ml. of 10% HCl. The product precipitated slowly. After stirring overnight at 25° C., the product was collected. The pH was 2.45. A second crop was obtained when enough HCl was added to lower the pH to 1. The two crops were combined, reslurried in 250 ml. of $H_2O$, collected, and redissolved in 500 ml. of water with NaOH. The solution was treated at pH 5 with charcoal at 25° C. and added to 255 ml. of conc. HCl at 25° C. After stirring 30 min. the slurry was filtered and the product was reslurried in 200 ml. of water and dried at 80° C. for 2 hrs. Yield of 5-acetamido-N-[tris(hydroxymethyl)methyl]-2,4,6-triiodoisophthalamic acid, 169.8 g. (63.8%), N.E. found/theory, 706.9/704.0. TLC in two systems produced in a single spot, (20μl of a 2% solution) (the systems were benzene: MEX: 88% formic acid; (60:25:20) and i-butyl alcohol: isopropyl alcohol: ammonium hydroxide (100:40:50).

EXAMPLE 6

The sodium salt of 5-acetamido-N-[tris(hydroxymethyl)methyl]-2,4,6-triiodoisophthalamic acid was prepared by conventional means. Its water solubility is about 48–50% w/v at 25° C.

EXAMPLE 7

A solution of the meglumine salt of 5-acetamido-N-[tris-(hydroxymethyl)methyl]-2,4,6-triiodoisophthalamic acid was prepared. Its solubility is greater than 60% w/v.

EXAMPLE 8

5-Nitro-N[2-(1,3-dihydroxy-2-methyl)propyl]-isophthalamic Acid

Methyl hydrogen 5-nitroisophthalate (169 g.; 0.75 mole) and 2-amino-2-methyl-1,3-propanediol (315 g.;3.0 mole) were mixed in 450 ml. of $H_2O$. After brief warming (60°, 30 min.), a clear solution was obtained. The solution was allowed to stir at room temperature for 20 hrs., and was then poured slowly into a stirred solution of $H_2O$ (280 ml.) and $H_2SO_4$ (120 ml.) with cooling. The product precipitated. After cooling in an ice-bath for 1 hr., the product was collected, slurried in $H_2O$ (1200 ml.) and recollected. TLC indicated the product contained a small amount of 5-nitroisophthalic acid. The product was then treated with hot water (70°, 1500 ml.) and was collected when the water was still hot. This treatment yielded essentially pure 5-nitro-N-[2-(1,3-dihydroxy-2-methyl) propyl]-isophthalamic acid (167 g.; 0.56 mole; 74.7% yield). Spectral data (I.R. NMR, mass spectroscopy) confirmed the structure. This material is suitable for use in the following (hydrogenation) step.

Recrystallization from $H_2O$ (1:20 w/v) or from $H_2O/CH_3OH$ yield a product melting at 184°–185° C.

EXAMPLE 9

5-Amino-N-[2-(1,3-dihydroxy-2-methyl) propyl]-2,4,6-triiodoisophthalamic Acid 5-Nitro-N-[2-(1,3-dihydroxy-2-methyl)-propyl]-isophthalamic acid (149.13 g.: 0.5 mole) was dissolved in dilute sodium hydroxide solution ($H_2O$, 400 ml.; 50% NaOH; 30 ml.). The solution was adjusted to pH 5.8 with acetic acid and was treated with charcoal (3.5 g.) and 5% Pd/C (1.4 g.). The solution was filtered, diluted to 625 ml. and b 5% Pd/C (3.3 g.) was added. Hydrogenation was then carried out in a Parr shaker at room temperature. Hydrogen uptake was almost complete in about 3 hrs. although shaking was continued overnight. The solution was then filtered, the filtrate was diluted to 1810 ml. and hydrochloric acid (95 ml.) was added. A solution of 2.34 N sodium iododichloride ($NaICl_2$; 705 ml., 1.65 mole) was added in portions at 45° with stirring. One hour after the addition of $NaICl_2$ was finished, the solution was diluted to twice its volume and the reaction temperature was raised to 80°–83° . During the course of the reaction, the product generally precipitated, and after reaction for 4 hrs. at this temperature, iodine uptake was 95% as determined by titration of an aliquot with standard sodium thiosulfate solution. At this point, $H_2O$ (1500 ml.) was added and the reaction (at 80°–83° ) was allowed to continue for another 30 minutes. While the solution was still hot, the precipitated 5-amino-N-[2-(1,3-dihydroxy-2-methyl)-propyl]-2,4,6-triiodoisophthalamic acid was collected and dried (Yield, 234.5 g.). The filtrate, after standing at room temperature overnight, gave another crop of the product (17 g.). The total product weighed 251.5 g. (0.389 mole; 77.8% yield). TLC indicated the product was essentially pure. IR and NMR spectra were in agreement with the structure proposed. Anal. Calcd. C, 22.31; H, 2.03; I, 58.94; N, 4.34; N.E. 645.94. Found: C, 22.50; H, 2.46; I, 58.79; N, 4.27; N.E. 650.32. The sodium salt of this acid is highy soluble in water (about 93% w/v).

EXAMPLE 10

5-Acetamido-N-[2-(1,3-dihydroxy-2-methyl) Propyl]-2,4,6-triiodoisophthalamic Acid A mixture of acetic anhydride (320 ml.) and $H_2SO_4$ (0.7 ml.) was warmed to 45° and 5-amino-N-[2-(1,- dihydroxy-2-methyl) propyl]2,4,6-triiodoisophthalamic acid (64.6 g., 0.1 mole) was added in portions with stirring so that the reaction temperature was maintained at 50°–55°. After the addition of the compound, the reaction temperature was raised to 55°–60° and the reaction was continued for 1 hour. The resulting slurry was stirred overnight at room temperature and was then poured slowly into a mixture of $H_2O$ (600 ml.) and ice (300 g.). After the solution was stirred for 30 minutes the resulting 5-acetamido-N-[2-(1,3-diacetoxy-2-methyl)-propyl]-2,4,6-triiodoisophthalamic acid was collected, slurried in $H_2O$ (800 ml.) and re-collected. The compound was then dissolved in dilute ammonia solution ($H_2O$, 340 ml. and 29% ammonia solution, 310 ml.) and the solution was stirred and heated at 65°–70° for 2 hours to hydrolyze the acetate ester groups the solution was cooled, filtered and poured slowly into an ice-cold mixture of $H_2O$ (300 ml.) and sulfuric acid (200 ml.) The 5-acetamido-N-[2-(1,3-dihydroxy-2-methyl)-propyl]-2,4,6triiodoisophthalamic acid precipitated, and was collected, slurried in $H_2O$ (100 ml.) and re-collected (47.4 g.; 0.069 mole; 69% yield). TLC, one spot. IR and NMR spectroscopy confirmed the structure. MP 270°–272° C. (decomp.). Anal. Calcd. $C_{14}H_{15}I_3N_2O_6$: C, 24.43; H, 2.20; I, 55.34; N, 4.07; N.E. 688.0. Found: C, 24.36; H, 2.28; I, 55.21; N, 4.06; N.E. 684.4.

EXAMPLE 11

5-Acetamido-N-[2-(1,3-dihydroxy-2-methyl)-propyl]-2,4,6-triiodoisophthalamic Acid, Sodium Salt The free acid product from the process of Example 10 (3 g.) was dissolved in a stoichiometric amount of sodium hydroxide solution. The water was evaporated under reduced pressure at 60° C. and the residual sodium salt was dried at 45° C. overnight. The absence of decomposition was indicated by TLC. The water solubility of the sodium salt of 5-acetamido-N-[2-(1,3-dihydroxy-2-methyl)-propyl]-2,4,6-triiodoisophthalamic acid thus prepared was found to be approximately 82% w/v.

EXAMPLE 12

5-Acetamido-2,4,6-triiodo-N-[tris (acetoxymethyl)methyl]isophthalamic Acid

5-Amino-2,4,6-triiodo-N-[tris(hydroxymethyl)methyl]isophthalamic acid (50.0 g., 0.076 mol.) was added in one portion to a stirred solution of sulfuric acid (0.36 ml.) in acetic anhydride (136.0 ml.). The temperature of the reaction mixture rose briefly to 82° and dissolution was effected. As the reaction mixture cooled to room temperature, the product began to precipitate at 47° and the mixture was diluted with toluene (100 ml.). The mixture was stirred at room temperature for 1 hr., and filtered. The filter cake was washed with toluene (50 ml.), dried, dissolved in hot methanol (300 ml.), and treated with charcoal (6 g.). After removal of the charcoal, the product precipitated from the cold station and was collected and dried (70°) to give white crystalline 5-acetamido-2,4,6-triiodo-N-[tris(acetoxymethyl)methyl]-isophthalamic acid (38.8 g.) m.p. 248–251 (dec., uncorr.). (Yield, 62%). This material was pure by TLC analysis (benzene, 2-butanone, 88% formic acid; 60:25:20) and its structure was confirmed by IR and NMR. Anal. Calcd. for $C_{20}H_{21}I_3N_2O_{10}$: C, 28.94; H, 2.55; N.E., 830.12. Found: C, 29.02; H, 2.70; N.E., 825.6.

EXAMPLE 13

Sodium 5-Acetamido-2,4,6-triiodo-N-[tris(acetoxymethyl)methyl]isophthalamate

A stirred slurry of 5-acetamido-2,4,6-triiodo-N-[tris(acetoxymethyl)methyl]isophthalamic acid (4.15 g., 5 mol.) in water (20 ml.) was carefully neutralized by dropwise addition of 1 N sodium hydroxide solution (5.00 ml.) so that the pH of the solution never exceeded 7.00. The resulting clear solution (pH 6.98) was concentrated under reduced pressure at room temperature (25°, 20 mm. to 0.1 mm.) and dried overnight in vacuo (0.1 mm.) to yield the salt indicated in the caption as a white powder (4.2 g.). The solubility of this powder in water is greater than or equal to 100% (wt/vol).

EXAMPLE 14

5-Acetamido-2,4,6-triiodo-N-[tris(acetoxymethyl)methyl]isophthalamyl Chloride

This acid chloride is prepared by stirring a cold solution of 5-acetamido-2,4,6-triiodo-N-[tris(acetoxymethyl)methyl]isophthalamic acid in dimethylacetamide with excess thionyl chloride. After stirring in the cold, the reaction mixture is allowed to warm, thus providing a solution of 5-acetamido-2,4,6-triiodo-N-[tris(acetoxymethyl)methyl]isophthalamyl chloride suitable for use as an intermediate, in situ. Alternatively, the product is isolated by concentrating the solution under reduced pressure to provide the acid chloride, which is dissolved in anhydrous tetrahydrofuran (THF). The THF solution is washed with cold, saturated sodium chloride solution and sodium bicarbonate solution and dried over sodium sulfate. Then the THF solution is concentrated to provide material which is suitable for use as an intermediate.

EXAMPLE 15

5-Amino-2,4,6-triiodo-N-[tris-(acetoxymethyl)methyl]-isophthalamic Acid

A mixture of 5-amino-2,4,6-triiodo-N-[tris(hydroxymethyl) methyl]isophthalamic acid and glacial acetic acid is heated in the presence of a catalytic amount of mineral acid (such as sulfuric acid or dry hydrogen chloride) or a dry cation exchange resin (strong acid form). Molecular sieves may be used to act as a water scavenger. After the reaction is complete the acid catalyst is neutralized, or in the case of use of molecular sieves and the cation-exchange resin, the reaction mixture is filtered. The solution is then concentrated in high vacuum to provide the desired 5-amino-2,4,6-triiodo-N-[tris(acetoxymethyl)methyl]isophthalamic acid in sufficient purity for use as an intermediate.

EXAMPLE 16

5-Amino-2,4,6-triiodo-N-[tris(acetoxymethyl)methyl]-isophthalamyl chloride

5-Amino-2,4,6-triiodo-N-[tris(acetoxymethyl)methyl]isophthalamic acid is heated briefly with excess thionyl chloride. The reaction mixture is then concentrated in vacuo and the concentrate is dissolved in tetrahydrofuran (THF) and washed with cold, saturated solutions of sodium bicarbonate and sodium chloride to hydrolyze the thionylamino group. The THF solution may be used for further reaction, or alternatively the 5-amino-2,4,6-triiodo-N-[tris(acetoxymethyl) methyl]-isophthalamyl chloride may be isolated by evaporating the solvent.

EXAMPLE 17

Methyl N-methyl-5-in nitro-N-[tris (hydroxymethyl)methyl]isophthalamate

Methoxy-carbonyl-5-nitrobenzoyl chloride [G. B. Hoey, et al., J. Med. Chem, 6, 24 (1963)] is added to a cold stirred slurry of N-methyl-tris(hydroxymethyl)methylamine and potassium carbonate in dimethylformamide to form a solution of N-methyl-5-nitro-N-[tris(-hydroxymethyl)methyl]isophthalamic acid, methyl ester.

EXAMPLE 18

N-Methyl-5-nitro-N-[tris(hydroxymethyl)methyl]-isophthalimic Acid

Methyl N-methyl-5-nitro-N-[tris(hydroxymethyl)methyl]isophthalamate is stirred with one equivalent of sodium hydroxide in aqueous methanol. The reaction mixture is concentrated to remove the methanol, diluted with water and acidified with mineral acid to provide crystalline N-methyl-5-nitro-N-[tris (hydroxymethyl)methyl]isophthalamic acid.

EXAMPLE 19

5-Amino-N-methyl-N-[tris(hydroxymethyl)methyl]-isophthalamic Acid

N-methyl-5-nitro-N[tris(hydroxymethyl)methyl]-isophthalamic acid is catalytically hydrogenated, generally as described in Example 2, to produce 5-amino-N-methyl-N-[tris(hydroxymethyl) methyl]isophthalamic acid.

EXAMPLE 20

5-Amino-2,4,6-triiodo-N-methyl-N-[tris(hydroxymethyl)methyl]isophthalamic Acid

5-Amino-N-methyl-N-[tris(hydroxymethyl)methyl]-isophthalamic acid is iodinated, generally as described in Example 3, to produce 5-amino-2,4,6-triiodo-N-methyl-N-[tris(hydroxymethyl) methyl]isophthalamic acid.

EXAMPLE 21

5-Acetamido-2,4,6-triiodo-N-methyl-N-[tris(hydroxymethyl)methyl]isophthalamic Acid 5-Amino-2,4,6-triiodo-N-methyl-N-[tris-(hydroxymethyl)methyl] isophthalamic acid is acetylated, generally as described in Example 5, to produce 5-acetamido-2,4,6-triiodo-N-methyl-N-[tris(hydroxymethyl)methyl]isophthalamic acid.

EXAMPLE 22

5-Acetamido-N-[(1,3-diacetoxy-2-methyl)-2-propyl]-2,4,6-triiodoisophthalamic Acid 5-Amino-N-[1,3-dihydroxy-2-methyl)-2-propyl]-2,4,6-triiodoisophthalamic acid (64.6 g., 0.1 mole) was added in portions to warm (45° C.) stirred acetic anhydride (320 ml.) and sulfuric acid (0.7 ml.) so that the reaction temperature was maintained at 50°–55° C. The reaction mixtutre was then stirred at 55°–60° for an hour, then overnight at room temperature, then it was poured slowly into a mixture of water (600 ml.) and ice (300 g.). After 30 minutes stirring, the product was collected, slurried in water (800 ml.), re-collected, and dried. TLC: one spot. IR and NMR are in agreement with the desired structure. Yield, 57g.(73.8%). A 53 g. portion of the product was slurried with ethyl acetate (400 ml.) and then with water (400 ml.) and dried. Yield of 5-acetamido-N-[(1,3-diacetoxy-2-methyl)-2-propyl]-2,4,6-triiodoisophthalamic acid, 47 g.; m.p. 269.7°–270.7° C. Anal. Calcd. for $C_{18}H_{19}I_3N_2O_8$: C, 28.00; H, 2.48; N.E. 772.05. Found: C, 28.01; H, 2.58; N.E. 763.7.

EXAMPLE 23

Sodium 5-acetamido-N-[(1,3-diacetoxy-2-methyl)-2-propyl]-2,4,6-triiodoisophthalamate 5-Acetamido-N-[(1,3-diacetoxy-2-methyl)-2-propyl]-2,4,6-triiodoisophthalamic acid (2.080 g.) was dissolved in a stoichiometric amount of 0.1032 N sodium hydroxide solution, the water was evaporated at 60° C. under reduced pressure, and the residual solid was dried at 45° C. overnight. The amorphous sodium 5-acetamido-N-[(1,3-diacetoxy-2-methyl)-2-propyl]-2,4,6-triiodoisophthalamate (2.05 g.) was dissolved in sufficient water to yield 2.0 ml. of solution (102.5% w/v). No crystallization occurred when the solution was allowed to stand at room temperature, thus indicating that the solubility of this sodium salt is greater than 100% w/v.

EXAMPLE 24

Methyl 5-amino-2,4,6-triiodo-N-[tris(acetoxymethyl) methyl]isophthalamate

A solution of 5-amino-2,4,6-triiodo-N-[tris(acetoxymethyl)methyl]isophthalamyl chloride in tetrahydrofuran (prepared as described in Example 16) is treated in the cold with methanol in the presence of sodium bicarbonate. After the esterification is complete, the reaction mixture is filtered to remove the inorganic salts and methyl 5-amino-2,4,6-triiodoN-[tris(acetoxymethyl)methyl]isophthalamate is isolated by evaporating the solvent under reduced pressure.

EXAMPLE 25

Ethyl 5-Acetamido-2,4,6-triiodo-N-[tris(hydroxymethyl)methyl]-isophthalamate A solution of 5-acetamido-2,4,6-triiodo-N-[tris-(acetoxymethyl) methyl]isophthalamyl chloride in tetrahydrofuran (prepared as described in Example 14) is heated with excess anhydrous ethanol to effect esterification of the acid chloride and transesterification of the acetate esters. After the reaction is complete, the solvent is removed under reduced pressure and the residue is recrystallized from ethanol to provide the desired ethyl 5-acetamido-2,4,6-triiodo-N-[tris-(hydroxymethyl) methyl]isophthalamate.

EXAMPLE 26

2,4,6-Triiodo-5-methoxyacetamido-N-[(trishydroxymethyl)-methyl]-isophthalamic Acid a. Methoxyacetyl chloride:

A solution of dimethylacetamide (420 ml.) containing methoxyacetic acid (95.4 g., 1.056 mole) was cooled to 0°–5° and thionyl chloride (125.7 g., 1.056 mole) was added dropwise so that the reaction temperature was maintained at 4°–8°. After the addition, the reaction mixture was stirred at 0°–5° for 2 hours. The solution of methoxyacetyl chloride was used in the next step.

b. 2,4,6-Triiodo-5-methoxyacetamido-N-[tris(methoxyacetoxymethyl) methyl]-isophthalamic Acid:

5-Amino-2,4,6-triiodo-N-[trishydroxymethyl)-methyl]-isophthalamic acid (72.9 g., 0.11 mole) was dissolved in dimethylacetamide (180 ml.) and was added dropwise at 5° C. to the methoxyacetyl chloride solution from step (a). After the addition of the amino compound, the reaction mixture was stirred at 5° for 1 hour before it was allowed to stir at room temperature overnight. Water (300 ml.) was added with cooling (solution temperature below 15°) and the solution was stirred for 1 hour. Dimethylacetamide and water were evaporated at 70° under vacuum and a viscous residue of 2,4,6-triiodo-5-methoxyacetamido-N-[tris(methoxyacetoxymethyl)methyl]-isophthalamic acid was obtained.

c. Ammonium 2,4,6-triiodo-5-methoxyacetamido-N-[tris (hydroxymethyl)-methyl]isophthalamate:

Water (100 ml.) was added to the residual product of step (b), followed by ammonium hydroxide (29% $NH_3$) until solution had a pH of 9.6; the solution was then heated at 70° for 2 hours with stirring to hydrolyze the methoxyacetoxy esters and form a solution of the salt indicated in the caption. The solution was cooled, acetic acid was added (to pH 5.8) and the solution was stirred with charcoal (3 g.) for 30 minutes and filtered.

d. 2,4,6-Triiodo-5-methoxyacetamido-N-[tris(hydroxymethyl) methyl]isophthalamic Acid:

The solution of ammonium 2,4,6triiodo-5-methoxyacetamido-N-[tris(hydroxymethyl)-methyl]isophthalamate from step (c) was poured into 6N hydrochloric acid (500 ml.). Hydrochloric acid (37% -- 200 ml.) was then added and the solution was allowed to stand at room temperature for 4 days until precipitation began. The solution was stirred to accelerate precipitation. The precipitate was collected and slurried in water (300 ml.); 50% sodium hydroxide was added until a clear solution was obtained. The solution was then acidified with acetic acid to pH 5, stirred for 20 minutes with charcoal (2 g.), filtered, and poured into a stirred solution of 6N HCl (600 ml.). The solution became cloudy and the product started to precipitate after 15 minutes. The 2,4,6-triiodo-5-methoxyacetamido-N-[tris(hydroxymethyl)methyl] isophthalamic acid was collected, twice slurried in water (200 and 120 ml.), collected and dried. M.P. 260.6°–262.6° (dec.). IR and NMR spectra were in agreement with the desired structure. The product weighted 35.5 g. (0.048 mole, 43.9%). TLC: one spot [ethyl acetate:methanol:acetic acid (10:5:1); isobutanol:isopropanol:ammonium hydroxide (10:4:4].

Anal. Calcd. for $C_{15}H_{17}I_3N_2O_8$: C, 24.54; H, 2.33; I, 51.87; N, 3.82; Neutral Equivalent, 734.01. Found: C, 24.34; H, 2.51; I, 51.52; N, 3.59; Neutral Equivalent, 737.01.

EXAMPLE 27

Sodium 2,4,6-triiodo-5-methoxyacetamido-N-[tris(hydroxymethyl)methyl]isophthalamate 2,4,6-Triiodo-5-methoxyacetamido-N-[tris(hydroxymethyl)methyl] isophthalamic acid (2.03 g.) was dissolved in a stoichiometric quantity of 0.1032 N NaOH. The solution was evaporated under reduced pressure at 60° C. and the residual sodium salt was dried at 45° C. overnight. The solubility of this sodium salt in water at 25° C. is approximately 67.4% (w/v). The following examples illustrate the use of certain compounds of the invention in the preparation of X-ray contrast media.

EXAMPLE 28

To a slurry of 361 g of 5-acetamido-N-[2-(1,3-dihydroxy-2-methyl)propyl]-2,4,6-triiodo-isophthalamic acid in 250 ml. of water, is added 59.5 g. of N-methylglucamine with stirring, followed by 7.8 g. of sodium hydroxide pellets. After the addition of 55 mg. of calcium disodium edetate (stabilizer), the mixture is adjusted to pH 7.4 using a solutioon of 3.1 g. of N-methylglucamine and 0.4 g. of sodium nydroxide in 75.6 ml. of water. Then 70 mg. of sodium dihydrogen phosphate is added with stirring, and the pH readjusted to 7.4. Dilution of the solution to 500 ml. provides a formulation containing 400 mg. of iodine per milliliter. The solution is subdivided into vials and sterilized by autoclaving.

EXAMPLE 29

To a slurry of 540 g. of 5-acetamido-2,4,6-triiodo-N-[tris (hydroxymethyl)methyl]-isophthalamic acid in 650 ml. of water at about 50° C. is added with stirring 116.60 g. of N-methylglucamine, 400 mg. of calcium disodium edetate, 2.47 g. of trisodium citrate dihydrate, and 1.26 g. of calcium oxide. The solution is then adjusted to pH 6-7 using 5N sodium hydroxide. The solution is iluted to a little less then 1,000 ml. and adjusted to pH 7.4using 0.1N sodium hydroxide. Finally the solution is diluted to exactly 1,000 ml. to provide a formulation containing 292 mg. iodine per milliliter. The solution is subdivided into vials and sterilized by autoclaving.

EXAMPLE 30

To a stirred slurry of 675 g. of 2,4,6-triiodo-5-methoxyacetamido-N-[tris(hydroxymethyl)-methyl]-isophthalamic acid in 600 ml. of water are added at 55° C., 1.03 g. of magnesium chloride hexahydrate, 2.31 g. of calcium chloride dihydrate, 20 g. of sodium hydroxide pellets, 52.2 g. of N-methylglucamine, 110 mg. of calcium disodium edetate, and 125 mg. of sodium dihydrogen phosphate. The formulation is then adjusted to pH 7.4 using a solution of 7.8 g. of N-methylglucamine and 3 g. of sodium hydroxide in 50 ml. of water. The pH adjustments are effected under a nitrogen atmosphere. After diluting to a final volume of a little less than 1,000 ml., the solution is stirred under nitrogen overnight at room temperature, readjusted to pH 7.4 the next day, and diluted to a final volume of 1,000 ml. This formulation contains 350 mg. iodine per milliliter. It is subdivided into ampuls and sterilized by autoclaving.

EXAMPLE 31

A buffered, stabilized solution of meglumine 5-acetamido-N-[2-(1,3-dihydroxy-2-methyl)propyl]2,4,6-triiodoisophthalamate is prepared by stirring sufficient meglumine (N-methylglucamine) into a slurry of 5-acetamido-N-[2-(1,3-dihydroxy-2-methyl) propyl]-2,4,6-triiodoisophthalamic acid (361 g.) in water (250 ml.) to dissolve the acid and provide neutral to faintly acid solution, adding calcium disodium edetate (55 mg.), making the solution faintly alkaline (pH 7.4) by the careful addition of a solution of megiumine, adding sodium dihydrogenphosphate (70 mg.) with stirring, readjusting the pH to 7.4 and diluting the solution to 500 ml. The resulting solution, containing 400 mg. of iodine per milliliter, is subdivided into vials and is sterilized by autoclaving.

EXAMPLE 32

A buffered stabilized solution of sodium 5-acetamido-2,4,6-triiodo-N-[tris(hydroxymethyl)methyl]isophthalamate is prepared by adding, with stirring, sufficient sodium hydroxide pellets to a slurry of 5-acetamido-2,4,6-triiodo-N-[tris(hydroxymethyl) methyl]isophthalamic acid (540 g.) in water (650 ml.) to dissolve the acid and provide a neutral to faintly acid solution, adding calcium disodium edetate (400 mg.), trisodium citrate dihydrate (2.47 g.), adjusting the pH to the range 6–7, if necessary, by titration with 5 N sodium hydroxide solution, diluting the solution to about 900–950 ml., titrating to pH 7.4 with 0.1 N sodium hydroxide, and finally adjusting the volume to exactly 1000 ml. The resulting solution, containing 292 mg. iodine per milliliter is subdivided into vials and is sterilized by autoclaving. Satisfactory intravenous urograms are obtained when any of the preparations described in Examples 28–32 is administered to dogs at a dosage of 350 mg. I/kg. Toxicity evaluations by three different techniques were carried out on solutions of the meglumine salts of three 5-acetamido-N-[poly(hydroxyalkyl)alkyl]2,4,6-triiodoisophthalamic acids of the invention. The techniques utilized are outlined below.

I. ACUTE INTRAVENOUS TOXICITY STUDIES IN MICE

Swiss Albino mice (Charles River) were dosed in the lateral tail vein with solutions of the iodinated compound containing 28.27% of iodine, injected at the rate of 1 ml/min. Following injections the animals were observed for immediate reactions and then daily throughout a seven day observation period. The $LD_{50}$ values were calculated by the method of Litchfield and Wilcoxon (J. of Pharmac. and Exptl. Therap. 96: 99–113, 1949).

II. INTRACEREBRAL TOXICITY IN MICE

Swiss Albino mice (Charles River) were used. Fixed volumes of solutions of various concentrations of the iodinated compounds were injected intracerebrally via a 27 gauge needle, ( inch length) according to the method of Haley, et al. (Br. J. of Pharmac. 12:12–15, 1957). The animals were observed immediately after injections and daily throughout a seven day observation period. The $LD_{50}$ values were calculated by the method of Litchfield and Wilcoxon (J. cf Pharmac. and Exptl. Therap. 96:99–113, (1949).

III. INTRACISTERNAL TOXICITY IN RATS

Sprague Dawley (Carworth) rats were used. The method used was a variation of the procedure outlined by Melartin et al. (Invest. Rad. 5:13–21, 1970). After dosing, the animals were housed individually, and observed for immediate reactions and periodically for a two day observation period. The LD$_{50}$ values were calculated according to the method of Litchfield and Wilcoxon, (J. of Pharmac. and Exptl. Therap. 96:99-115, 1949).

The results of the toxicity evaluations made on solutions of three meglumine salt compounds of the invention are set forth in Table 1, together with comparable values obtained with solutions of the meglumine salts of the previously known compounds, iothalamic acid (5-acetamido-2,4,6-triiodo-N-methylisophthalamic acid — U.S. Pat. No. 3,145,197), and 5-acetamido-2,4,6-triiodo-N-(2-hydroxyethyl)-isophthalamic acid (U.S. Pat. Nos. 3,622,616; 3,702,866).

Table 1

Toxicity Values for Meglumine Salts of Five 5-Acetamido-2,4,6-Triiodoisophthalamic Acids

| Triiodoisophthalamic Acid | LD$_{50}$ of Meglumine Salt* | | |
|---|---|---|---|
| | I.V. (Mice) | Intracerebral (Mice) | Intracisternal (Rats) |
| Acid of Examples 4(A) and 5(i) | (a) 6148 (b) 6200 | 700 638 | 151 |
| Acid of Example 10(ii) | 4650 790 | 242 | |
| Acid of Example 26(d) (iii) | | abt. 650 | abt. 150 |
| Iothalamic Acid | 5742 | 280 | 86 |
| 5-Acetamido-2,4,6-triiodo-N-(2-hydroxyethyl)-isophthalamic acid | 5812 | 174 | 49 |

(i)5-Acetamido-N-[tris-(hydroxymethyl)methyl]-2,4,6-triiodoisophthalamic acid.
(ii)5-Acetamido-N-[2-(1,3-dihydroxy-2-methyl)-propyl]-2,4,6-triiodoisophthalamic acid.
(iii)2,4,6-Triiodo-5-methoxyacetamido-N-[tris-(hydroxymethyl)methyl]isophthalamic acid.
*All LD$_{50}$ values are expressed in terms of mg. contained iodine/kg. animal body weight.

The excellent toxicity data obtained by the intracerebral and intracisternal routes for the three novel compounds in Table I indicates that they are particularly suitable for use as x-ray contrast agents in the visualization of cerebrospinal cavities.

Although the 5-amino-2,4,6-triiodo-N-[poly(hydroxyalkyl) alkyl]isophthalamic acids and the 5-acylamino-2,4,6-triiodo-N-[poly(acyloxyalkyl)alkyl]-isophthalamic acids of the invention are of interest primarily as intermediates, as disclosed herein, they have toxicity characteristics which are comparable, in some instances, with those of established water-soluble contrast agents.

It will be understood that in addition to the compounds specifically disclosed in the above examples, other compounds within the scope of the invention may be prepared by the same general methods.

In view of the above, it will be seen that the several objects of the invention are achieved and other advantageous results obtained.

As various changes could be made in the above products and methods without departing from the scope of the invention, it is intended that all matter contained in the above description shall be interpreted as illustrative and not in a limiting sense.

What is claimed is:

1. A compound having the formula:

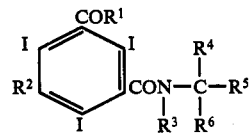

wherein
R$^1$ is hydroxy, or OM, M being a pharmaceutically acceptable cation,
R$^2$ is an acetamido or methoxyacetamido function,
R$^3$ is hydrogen, R$^4$ is a methyl or hydroxymethyl function and each R$^5$ and R$^6$ is a hydroxymethyl function 2. A compound according to claim 1 wherein R$^1$ is hydroxy.

3. A compound according to claim 1 wherein R$^1$ is OM, M being sodium.

4. A compound according to claim 1 wherein R$^1$ is OM, M being meglumine.

5. A compound according to claim 2 wherein R$^2$ is acetamido and each R$^4$, R$^5$ and R$^6$ is hydroxymethyl.

6. A compound according to claim 3 wherein R$^2$ is acetamido and each R$^4$, R$^5$ and R$^6$ is hydroxymethyl.

7. A compound according to claim 4 wherein R$^2$ is acetamido and each R$^4$, and R$^5$ and R$^6$ is hydroxymethyl.

8. A compound according to claim 2 wherein R$^2$ is methoxyacetamido and each R$^4$, R$^5$ and R$^6$ is hydroxymethyl.

9. A compound according to claim 3 wherein R$^2$ is methoxyacetamido and each R$^4$, and R$^5$ and R$^6$ is hydroxymethyl.

10. A compound according to claim 4 wherein R$^2$ is methoxyacetamido and each R$^4$, R$^5$ and R$^6$ is hydroxymethyl.

11. A compound according to claim 2 wherein R$^2$ is acetamido, R$^4$ is methyl and each R$^5$ and R$^6$ is hydroxymethyl.

12. A compound according to claim 3 wherein R$^2$ is acetamido, R$^4$ is methyl and each R$^5$ and R$^6$ is hydroxymethyl.

13. A compound according to claim 4 wherein R$^2$ is acetamido, R$^4$ is methyl and each R$^5$ and R$^6$ is hydroxymethyl.

* * * * *